United States Patent [19]

Vijverberg

[11] 4,246,607
[45] Jan. 20, 1981

[54] X-RAY FLUOROSCOPY DEVICE

[75] Inventor: Gerardus P. M. Vijverberg, Eindhoven, Netherlands

[73] Assignee: U.S. Philips Corporation, New York, N.Y.

[21] Appl. No.: 18,546

[22] Filed: Mar. 8, 1979

[30] Foreign Application Priority Data

Mar. 16, 1978 [NL] Netherlands .......................... 7802858

[51] Int. Cl.³ ............................................. H04N 5/32
[52] U.S. Cl. ...................................... 358/111; 358/93; 358/183; 250/416 TV; 128/653
[58] Field of Search .................. 358/110, 111, 113, 97, 358/224, 226, 182, 93, 181, 100, 106, 183; 250/416 TV; 364/414; 128/653, 659, 654

[56] References Cited

U.S. PATENT DOCUMENTS

| 3,130,267 | 4/1964 | Engler | 358/224 |
| 3,730,985 | 5/1973 | Whitney | 358/113 |
| 3,806,633 | 4/1974 | Coleman | 358/113 |
| 4,157,572 | 6/1979 | Kennedy et al. | 358/111 |

FOREIGN PATENT DOCUMENTS 1210720 10/1970 United Kingdom ..................... 358/111

Primary Examiner—Robert L. Griffin
Assistant Examiner—Edward L. Coles
Attorney, Agent, or Firm—T. A. Briody; R. T. Mayer; J. E. Haken

[57] ABSTRACT

An X-ray fluoroscopy device comprises a television camera for locating the irradiation field. This camera forms an optical image of the object to be irradiated. This image can be displayed on a television monitor, together with an image of the irradiation field, so that the position of the irradiation field within the object can be directly observed.

6 Claims, 1 Drawing Figure

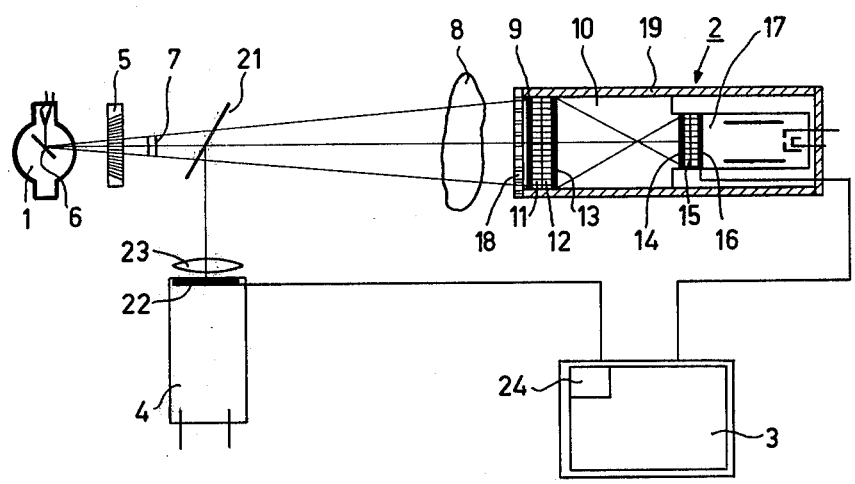

X-RAY FLUOROSCOPY DEVICE

The invention relates to an X-ray fluoroscopy device, comprising an X-ray source, an image intensifier, a television camera tube, and a television monitor for the display of an image of a part of an object.

A device of this kind is used, for example, for routine examinations, catherisation, surgery, neuroradiography and so on, where it is important to obtain a high-quality image of, for example, a comparatively small radiation zone within a larger anatomic unit. In modern versions, an X-ray image intensifier tube and a television camera tube are coupled to a fibre-optical window, so that a very sensitive high-quality image formation can be realized. Notably when use is made of an X-ray intensifier having a comparatively small entrance detection screen, which is attractive in order to obtain high resolution, a drawback consists in that the radiologist requires a comparatively long period of time for localizing the radiation image displayed within the anatomic unit. Not only is a substantial amount of time thus lost, but the patient is also exposed to radiation for a period of time which is longer than required for the actual image formation. For example, it has been found in practice that when use is made of a 5 cm image intensifier entrance screen 75 to 90% of the overall exposure time is used for locating the image. In X-ray exposures made, for example, by Bucky techniques, similar drawbacks occur in that the localizing of a sub-zone to be irradiated must be performed by means of a light viewfinder.

The invention has for its object to provide an X-ray fluorescopy device in which the localization time can be substantially reduced to, for example, only 10% of the total fluoroscopy time, while optimum image formation is maintained. To this end, an X-ray fluoroscopy device of the described kind in accordance with the invention is characterized in that the device comprises a second television camera for the display of a readily recognizable optical image of the object which covers the area to be irradiated.

Because an optical image of the object to be examined is displayed in an X-ray examining device in accordance with the invention by means of the second television chain which acts as a viewfinder, the location of the zone to be irradiated therein can be simply observed.

In a preferred embodiment in accordance with the invention, both images are simultaneously displayed on the same monitor, so that the irradiation field is directly localized in the object.

A further preferred embodiment comprises a monitor for the irradiation image as well as a monitor for the optical image of the environment. On the latter monitor the irradiation image or the contours thereof are also displayed. Complete freedom then exists for manipulation with the irradiation image displayed on the first monitor.

Some preferred embodiments in accordance with the invention will be described in detail hereinafter with reference to the accompanying diagrammatic drawing.

The drawing diagrammatically shows an X-ray fluoroscopy device, comprising an X-ray tube 1, an X-ray image intensifier/television camera system 2, a television monitor 3, and a second television camera 4. The embodiment shown comprises only a single television monitor on which both images are displayed in a superposed manner, an image thus being formed of, for example, a hand within which the irradiation field is localized. It is alternatively possible to use a separate television monitor for each of the television cameras, for example, the contours of the irradiation field of the first camera then being displayed on the monitor for the optical image. The advantage thereof consists in that the image on the two monitors can be individually adjusted, so that no information of the fluoroscopy image is lost or becomes difficult to observe, this is liable to occur when the two images are combined. The magnification, the contrast etc. of particularly the fluoroscopy image can thus be freely adjusted on the appropriate monitor, while a fixed indication of the irradiation field on the other monitor is maintained. A customary collimator 5 is associated with the X-ray source 1. An X-ray beam 7 emerges from a target anode of the X-ray tube 6 and after having passed through a part of an object 8 is incident on an entrance detection screen 9 of an image intensifier tube 10. Preferably the beam 7 has an angle of divergence such that it exactly covers the effective part of the entrance detection screen. The entrance detection screen of the image intensifier tube has a diameter of, for example, 5 cm and preferably contains CsI activated by, for example, Th as the luminescent material. In the described preferred embodiment, the luminescent material is provided on a fibre-optical screen 11 which is coupled to a (preferably also fibre-optical) entrance screen 12 of the image intensifier tube 10. On the inner side, the entrance window supports a photocathode 13 which preferably has a concave geometry, viewed from the inside. An electron beam emitted by the photocathode is displayed on an output luminescent screen 14, in this case reduced in diameter by only a factor 2. A light image thus transmitted is projected directly onto a target 16 of a television camera tube 17, again by means of a fibre-optical coupling 15. An image signal derived from the camera tube 17 is displayed on the monitor 3. A customary scattered radiation grid 18 may be arranged between the object 8 and the entrance screen/detection screen 9. A scattered radiation grid of this kind contains, for example, a heavy metal for absorbing scattered radiation in the X-ray beam as well as ferromagnetic material for shielding against disturbing magnetic fields. A surrounding sleeve 19 may have a shielding function against electrical and magnetic stray fields in addition to a structural function.

In a preferred embodiment in accordance with the invention, a mirror 21 is arranged in the X-ray beam 7. The mirror 21 should have a high transmission and a comparatively low dispersion for the X-radiation to be used. This can be achieved, for example, by utilizing a foil of a comparatively light element which is as thin as possible but which is sufficiently rigid, said foil being suitably optically reflective on the side facing the object.

Light reflected from the object 8 is projected onto an entrance screen 22 of the television camera 4 by the mirror 21. When an entrance optical system 23 of this television camera is panoramic, i.e. the camera has a comparatively large angle of aperture, the entire object or at least a readily recognizable part thereof can be intercepted and displayed, in this case again on the monitor 3. Alternatively this optical image can be displayed on a separate monitor on which geometrical data of the irradiation field are also projected. When the entrance optical system 23 of the camera 4 has a fixed or permanently adjustable focus, a fixed relationship with the angle of aperture of the X-ray beam can be assured as a result of the fixed image angle, so that the irradiation field is always displayed as a fixed contour, normally a circle, on the monitor for the optical image. The associated large depth of focus of the entrance optical system is a favourable side-effect for imaging. By the addition of an adjusting mechanism, adaptation to variations in the distance between the X-ray source 6 and the object 8 or the entrance detection screen 9 can be realized.

In a further preferred embodiment in accordance with the invention, the X-ray fluoroscopy device is designed for Bucky-examination methods. In known Bucky devices, use is made of a light viewfinder for localizing the part of the body to be irradiated; this viewfinder is comparatively expensive and involves rather difficult adjustment and also necessitates marking of the patient. When the viewfinder is replaced by a second television camera in accordance with the invention, the optical image can again be displayed on a monitor together with the radiation field in order to achieve fast and accurate localizing. Whenever a second monitor was mentioned in the foregoing, use could also be made of a monitor on which a partial image can be displayed, for example, as denoted by a partial image 24.

What is claimed is:

1. An X-ray fluoroscopy device for displaying an image of a part of an object comprising:
   an X-ray source disposed to irradiate an area of the object;
   an image intensifier disposed to intensify an image of X-rays from the source which pass through the object;
   a first television camera tube disposed to receive a first image from the output of the image intensifier;
   a first television monitor connected to display the first image from the first camera tube; and
   a second television camera disposed and connected to display an optical image of the object, which optical image includes the area of the object irradiated by the X-ray source;
   wherein the image intensifier includes an entrance detection screen and an exit screen, a transverse dimension of the entrance screen being not more than a few times the transverse dimension of the exit screen.

2. An X-ray fluoroscopy device for displaying an image of a part of an object comprising:
   an X-ray source disposed to irradiate an area of the object;
   an image intensifier disposed to intensify an image of X-rays from the source which pass through the object;
   a first television camera tube disposed to receive a first image from the output of the image intensifier;
   a first television monitor connected to display the first image from the first camera tube; and
   a second television camera disposed and connected to display an optical image of the object, which optical image includes the area of the object irradiated by the X-ray source;
   the output of the second television camera being connected to the first monitor so that the first image and the optical image are displayed on the same television monitor.

3. An X-ray fluoroscopy device for displaying an image of a part of an object comprising:
   an X-ray source disposed to irradiate an area of the object;
   an image intensifier disposed to intensify an image of X-rays from the source which pass through the object;
   a first television camera tube disposed to receive a first image from the output of the image intensifier;
   a first television monitor connected to display the first image from the first camera tube;
   a second television camera disposed and connected to display an optical image of the object, which optical image includes the area of the object irradiated by the X-ray source; and
   means for applying geometrical information from the first image and the output of the second television camera to the same television monitor so that geometric information from the first image is displayed on the same monitor as the optical image.

4. An X-ray fluoroscopy device as claimed in claim 3, wherein the second camera comprises a panoramic optical system having a permanently adjustable focus.

5. An X-ray fluoroscopy device as claimed in claim 4 wherein the second television camera includes adjusting means which measure the distance between the X-ray source and the object and adjust the focus of the second camera in response thereto.

6. An X-ray fluoroscopy device as claimed in claims 2, 3, 4, or 5 wherein the image intensifier comprises an entrance detection screen and an exit screen, a transverse dimension of the entrance screen being not more than a few times the transverse direction of the exit screen.

* * * * *